US007049001B2

(12) United States Patent
Häberle et al.

(10) Patent No.: US 7,049,001 B2
(45) Date of Patent: May 23, 2006

(54) CARBODIIMIDES WITH CARBOXYL OR CARBOXYLATE GROUPS

(75) Inventors: Karl Häberle, Speyer (DE); Ulrike Licht, Mannheim (DE); Sabine Kielhorn-Bayer, Maxdorf (DE); Christian Lach, Bad Dürkheim (DE); Bernd Meyer-Roscher, Nuestadt (DE); Robert Shane Porzio, Mannheim (DE); Christelle Staller, Seltz (FR); Peter Weyland, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 268 days.

(21) Appl. No.: 10/169,070

(22) PCT Filed: Jan. 5, 2001

(86) PCT No.: PCT/EP01/00057

§ 371 (c)(1),
(2), (4) Date: Jul. 5, 2002

(87) PCT Pub. No.: WO01/51535

PCT Pub. Date: Jul. 19, 2001

(65) Prior Publication Data

US 2003/0088030 A1    May 8, 2003

(30) Foreign Application Priority Data

Jan. 11, 2000    (DE) ................................ 100 00 656

(51) Int. Cl.
*B32B 27/00* (2006.01)
*C08G 73/10* (2006.01)
*C08G 18/72* (2006.01)

(52) U.S. Cl. .................. 428/423.1; 528/322; 528/310; 528/84

(58) Field of Classification Search ............. 428/423.1; 528/48, 52, 84, 310, 322
See application file for complete search history.

(56) References Cited

U.S. PATENT DOCUMENTS

| 3,502,722 | A | | 3/1970 | Neumann |
| 4,616,061 | A | * | 10/1986 | Henning et al. ............ 524/591 |
| 4,910,339 | A | | 3/1990 | Henning et al. |
| 5,276,096 | A | | 1/1994 | Serdiuk et al. |
| 5,866,715 | A | | 2/1999 | Tsai |
| 6,121,406 | A | | 9/2000 | Imashiro et al. |
| 6,194,500 | B1 | | 2/2001 | Imashiro et al. |
| 6,395,824 | B1 | * | 5/2002 | Beutler et al. .............. 524/591 |
| 6,610,784 | B1 | | 8/2003 | Overbeek et al. |
| 6,730,807 | B1 | * | 5/2004 | Haberle et al. ............. 562/439 |

FOREIGN PATENT DOCUMENTS

| CA | 2 384 873 | 5/2001 |
| DE | 1 130 594 | 5/1962 |
| DE | 1 156 401 | 10/1963 |
| DE | 195 21 500 | 6/1996 |
| DE | 198 21 668 | 11/1999 |
| DE | 199 54 006 | 5/2001 |
| EP | 0 198 343 | 10/1986 |
| EP | 0 686 626 | 12/1995 |
| EP | 0 952 146 | 10/1999 |
| EP | 0 962 490 | 12/1999 |
| GB | 851 936 | 10/1960 |
| GB | 1 083 410 | 9/1967 |

OTHER PUBLICATIONS

Copending U.S. Appl. No. 10/372,150.*
Beyer/Walter Lehrbuch der organischen Chemie 19. Auflage, S. Hirzel Verlag Stuttgart, S. 262 ff.
Derwent Abstract, AN 2000-014370, DE 198 21 668, Nov. 18, 1999.
A. Williams, et al., Chem. Rev., vol. 18, No. 4, pp. 589-636, "Carbodiimide Chemistry: Recent Advances", 1981.
J. W. Taylor, et al., ACS Symposium Series 663, pp. 137-163. "The Application of Carbodiimide Chemistry to Coatings", 1997.
J. W. Taylor, et al., Progress in Organic Coatings, vol. 35, pp. 215-221, "A Study on the Chemistry of Alkylcarbodiimide Ethylmethacrylates as Reactive Monomoers for Acrylic and Vinyl Ester-Based Latexes", 1999.
H. H. Pham, et al., Journal of Polymer Science Part A, Polymer Chemistry, vol. 38, pp. 855-869, "Synthesis, Characterization, and Stability of Carbodiimide Groups in Carbodiimide-Functionalized Latex Dispersions and Films", 2000.
H. H. Pham, et al., Macromolecules, vol. 32, pp. 7692-7695, "Polymer Interdiffusion vs. Cross-Linking in Carboxylic Acid-Carbodiimide Latex Films", 1999.
H. H. Pham, et al., ACS Symposium Series 790, pp. 88-102, "Film Formation From Blends of Carbodiimide and Carboxylic Acid Functional Latex", 2001.

(Continued)

*Primary Examiner*—Thao T. Tran
(74) *Attorney, Agent, or Firm*—Oblon, Spivak, McClelland, Maier & Neustadt, P.C.

(57) ABSTRACT

Compounds with carbodiimide units and carboxyl or carboxylate groups (compounds V), derived from
a) aliphatic or araliphatic $C_4$ to $C_{20}$ polyisocyanates (component a)
b) hydroxy carboxylic acids or hydroxy carboxylic salts (component b) and
c) if desired, further compounds, carrying groups able to react with isocyanate groups in an addition reaction (component c)
d) if desired, other isocyanates (component d),
the carbodiimide units being derived essentially exclusively from the isocyanate groups of component a).

11 Claims, No Drawings

OTHER PUBLICATIONS

A.H. M. Schotman, Recl. Trav. Chim. Pays-Bas, vol. 110, pp. 319-324, "Mechanism of the Reaction of Carbodiimides with Carboxylic Acids", 1991.

M. Ooka, et al., Progress in Organic Coatings, vol. 23, pp. 325-338, "Recent Developments in Crosslinking Technology for Coating Resins", 1994.

W. T. Brown, Journal of Coatings Technology, vol. 72, No. 904, pp. 63-70, "Effect of Crosslinker Reaction Rate on Film Properties for Thermoset Coatings", May 2000.

J. M. Geurts, Thesis, Eindoven University of Technology, "Lattices with Intrinsic Crosslink Activity", 1997.

* cited by examiner

CARBODIIMIDES WITH CARBOXYL OR CARBOXYLATE GROUPS

The invention relates to compounds having carbodiimide units and carboxyl or carboxylate groups (compounds V), derived from
a) aliphatic or araliphatic $C_4$ to $C_{20}$ polyisocyanates (component a)
b) hydroxy carboxylic acids or hydroxy carboxylic salts (component b) and
c) if desired, further compounds, carrying groups able to react with isocyanate groups in an addition reaction (component c)
d) if desired, other isocyanates (component d), the carbodiimide units being derived essentially exclusively from the isocyanate groups of component a).

Organic carbodiimides and their use as additives to aqueous polymer dispersions are known. They are added, for example, to polymer dispersions in order to increase the molecular weight of the polymers. In order to be able to disperse the carbodiimides simply and homogeneously in the dispersion, they are provided with hydrophilic groups.

EP-A-198 343 describes carbodiimides which carry sulfonate groups and also, if desired, polyethylene oxide units.

EP-A-686 626, moreover, discloses carbodiimides in which the hydrophilicity is brought about by ammonium groups, which are introduced by way of dialkylamino alcohols, by sulfonate groups, which are introduced by way of salts of hydroxy-functional alkylsulfonic acids, or by polyethylene oxide radicals.

The abovementioned products, however, have the following disadvantages:

Cationic products, such as carbodiimides hydrophilicized by ammonium groups, are incompatible with the anionically stabilized dispersions that are usually used.

The carbodiimides hydrophilicized with sulfonate groups are difficult to prepare. Owing to the highly lipophobic nature of the starting salts used, the reaction with the hydrophobic isocyanato-containing precursors is extremely difficult, since their mutual solubility is very low.

The dispersions cured using carbodiimides hydrophilicized with polyalkylene oxide radicals possess an undesirable permanent hydrophilicity.

DE-A-19821668 discloses carbodiimides based on 1,3-bis(1-methyl-1-isocyanatoethyl)benzene in which the hydrophilicization is brought about using amino sulfonic acids.

DE-A-19954006, unpublished at the priority date of the present specification, discloses carbodiimides based on aliphatic or aromatic polyisocyanates where the hydrophilicization is brought about using amino carboxylic acids.

It is an object of the present invention to provide carbodiimides which are compatible with the customary, anionically stabilized polymer dispersions, are simple to prepare, and do not impart additional permanent hydrophilicity to the dispersion films cured with them.

We have found that this object is achieved by the compounds (V) described at the outset.

The compounds (V) contain preferably from 200 to 2000 mmol/kg, with particular preference from 500 to 1800 mmol/kg, of carboxyl or carboxylate groups, based on the weight of the carbodiimides.

The carbodiimide group content is generally from 0.05 to 8, preferably from 0.10 to 5, mol/kg, based on the weight of the carbodiimides.

The carbodiimide units in the carbodiimides of the invention are essentially each formed by the coming together of any two NCO groups of component (a) with elimination of carbon dioxide to form one carbodiimide unit.

The compounds (V) preferably contain at least one carbodiimide unit, more preferably more than one carbodiimide unit; with particular preference, the average degree of condensation (number average), i.e., the average number of carbodiimide units in the carbodiimides of the invention, is from 1 to 20, in particular from 2 to 15.

Suitable monomers (a) are the aliphatic or araliphatic isocyanates having 4 to 20 carbon atoms that are commonly used in polyurethane chemistry.

Mention may be made in particular of diisocyanates $X(NCO)_2$, where X is an aliphatic hydrocarbon radical having 4 to 12 carbon atoms, a cycloaliphatic hydrocarbon radical having 6 to 15 carbon atoms, or an araliphatic hydrocarbon radical having 7 to 15 carbon atoms. Examples of such diisocyanates are tetramethylene diisocyanate, hexamethylene diisocyanate, dodecamethylene diisocyanate, 1,4-diisocyanatocyclohexane, 1-isocyanato-3,5,5-trimethyl-5-isocyanatomethylcyclohexane (IPDI), 2,2-bis(4-isocyanatocyclohexyl)propane, trimethylhexane diisocyanate, 1,4-diisocyanatobenzene, 1,3-bis(1-methyl-1-isocyanatoethyl) benzene (TMXDI), the isomers of bis(4-isocyanatocyclohexyl)methane (HMDI), such as the trans/trans, the cis/cis and the cis/trans isomers, and mixtures of these compounds.

The carbodiimides of the invention therefore preferably contain units of the formula I

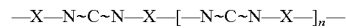

where
X is as defined above, and
n is an integer from 0 to 10, preferably from 0 to 5.

With particular preference, X is derived from TMXDI or hexamethylene diisocyanate.

Suitable hydroxy carboxylic acids are, for example, those specified in Beyer, Lehrbuch der Organischen Chemie, 19$^{th}$ edition on p. 262 ff.

Although acids with aromatically attached hydroxyl groups are also suitable, acids with aliphatically attached hydroxyl groups are preferred. Particular preference is given to hydroxy carboxylic acids having a hydroxyl group in the beta position, such as beta-hydroxypropionic acid or, with particular preference, hydroxypivalic acid, or alpha,alpha-hydroxymethylalkanoic acids such as dimethylolpropionic acid, for example.

Where the hydroxy carboxylic acids are used in the form of their salts, particularly suitable salts are alkali metal, alkaline earth metal, or ammonium salts.

Preferred compounds (V) are those of the formula II

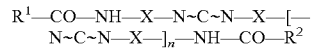

where n and X are as defined for formula I and $R^1$ and $R^2$ are radicals derived from component (b) by abstraction therefrom of a hydrogen atom attached to a hydroxyl group.

In addition to the structural units derived from components (a) and (b), the compounds (V) may, if desired, further comprise other structural units, which are derived from components (c) and (d) and comprise primarily urethane or urea units. These are formed by reacting the isocyanate groups of component (d) with the isocyanate-reactive groups of component (c) or with the amino groups of component (b) or by reacting the isocyanate-reactive groups of component (c) with the isocyanate groups of component (a). Therefore, the structural units of the formula I are interrupted or terminated by the structural units derived from components (c) and (d) or are located between a structural unit formed from components (a) and (b). Components (c) and (d) therefore serve primarily to regulate the molecular weight, since components (c) and (d) act primarily as the chain extender or chain terminator.

Components (c) carry groups which are able to react with isocyanate groups in an addition reaction. It is possible, for example, to use common substances which by virtue of their reaction with isocyanates produce urethane or urea groups. It is possible, for example, to use aromatic, aliphatic or araliphatic compounds having 1 to 20 carbon atoms, containing hydroxyl and/or amino groups as isocyanate-reactive groups. Preferred compounds having at least two isocyanate-reactive groups are organic compounds having at least two hydroxyl groups, having at least two amino groups, and/or at least one hydroxyl group and at least one amino group. Examples of those which it is possible to use are the following: aromatic, araliphatic and/or aliphatic polyols having 2 to 20 carbon atoms, preferably those having primary hydroxyl groups. Examples that may be mentioned include the following: 1,2-ethanediol, 1,3-propanediol, 1,2-propanediol, 1,4-, 2,4- and/or 2,3-butanediol, 1,5-pentanediol, 1,6-hexanediol, 1,7-heptanediol, 1,8-octanediol, 1,10-decanediol, neopentyl glycol, 2-methyl-1,3-propanediol, 2- and 3-methyl-1,5-pentanediol, polyethylene glycols, polypropylene glycols, preferably having two hydroxyl groups, the isomers of bis(hydroxy-methyl- or -ethyl)benzene, hydroxyalkyl ethers of dihydroxybenzenes, trimethylolpropane, glyceryl, pentaerythritol, or sugars having, for example, 4, 5 or 6 hydroxyl groups.

If isocyanate-reactive compounds which have ethylene oxide units are used, the fraction of ethylene oxide units in the carbodiimides of the invention should be preferably from 1 to 15% by weight, based on the weight of the carbodiimides. Preferably, no such compounds are used.

Amines to be used are amines having at least two primary and/or secondary amino groups. Examples that may be mentioned include the following: amines of the molecular weight range from 32 to 500 g/mol, preferably from 60 to 300 g/mol, which have at least two primary, at least two secondary, or at least both one primary and one secondary amino group. Examples of these are diamines such as diaminoethane, diaminopropane, diaminobutane, diaminopentane, diaminohexane, piperazine, 2,5-dimethylpiperazine, 1-amino-3,3,5-trimethyl-5-aminomethylcyclohexane, (isophoronediamine, IPDA), 4,4'-diaminodicyclohexylmethane, 1,4-diaminocyclohexane, aminoethylethanolamine, hydrazine, hydrazine hydrate, or triamines such as diethylenetriamine or 1,8-diamino-4-aminomethyloctane.

It is also possible to use amines derived from the above-mentioned amines by the substitution of one or more primary amino groups with further substituents, such as alkyl groups, for example, to give secondary amino groups. It is further also possible to use compounds having both at least one hydroxyl group and at least one amino group, examples being ethanolamine, propanolamine, isopropanolamine, aminoethylethanolamine, or N-alkyl amines derived therefrom.

Preference is given to the use of linear alcohols, amines or amino alcohols, particular preference to those having an even number of carbon atoms. Also preferred are alcohols, amines or amino alcohols containing cyclic structural elements.

If desired, it may be judicious, in addition to the above-described, isocyanate-reactive compounds having at least two functional groups, to use monofunctional compounds as well, in order to regulate the molecular weight of the carbodiimides of the invention, especially if the diisocyanates are reacted to the carbodiimides in a first step and then the isocyanato-containing carbodiimides are reacted with the isocyanate-reactive compounds. Monofunctional, isocyanate-reactive compounds which can be used are, for example, amines and, preferably, alcohols. Suitable amines, e.g., primary or preferably secondary amines, advantageously possess 1 to 12 carbon atoms, preferably 2 to 8 carbon atoms. Examples that may be mentioned include methyl-, ethyl-, propyl-, butyl-, pentyl-, hexyl-, 2-ethylhexyl-, octyl-, decyl-, diethyl-, dipropyl-, dibutyl-, methylbutyl-, ethylbutyl- and ethylhexylamine and also cyclohexylamine and benzylamine. To satisfy the isocyanate groups it is preferred, however, to use alcohols, e.g., primary or secondary alcohols of from 1 to 18 carbon atoms, preferably from 2 to 8 carbon atoms. Examples of primary or secondary alcohols that may be mentioned include the following: methanol, ethanol, n-propanol, isopropanol, n-butanol, sec-butanol, n-pentanol, technical-grade pentanol mixtures, n-hexanol, technical-grade hexanol mixtures, 2-ethylhexanol, octanol, 2-ethyloctanol, decanol and dodecanol, and also cyclohexanol and benzyl alcohol.

Component (b) is preferably used with monofunctional compounds, with particular preference monoamines.

In general, the molecular weight of components (c) is less than 400; in particular, the carbodiimides of the invention are free from units derived from macropolyols such as polyether polyols or polyester polyols having a molecular weight of more than 400.

Suitable components (d) are primarily aromatic isocyanates, e.g., 1,4-diisocyanatobenzene, 2,4-diisocyanatotoluene, 2,6-diisocyanatotoluene, 4,4'-diisocyanatodiphenylmethane or 2,4'-diisocyanatodiphenylmethane.

In general, the proportion of components (c) and (d), based on the proportion of all components (a) to (d) used to prepare the compounds V is not more than from 0 to 40% by weight, preferably from 0 to 30% by weight.

The carbodiimides of the invention are prepared essentially by two reaction steps, by
I. preparing carbodiimides having terminal isocyanate groups, by carbodiimidizing some of the isocyanate groups of component (a), and
II. reacting the compounds prepared in step I, having terminal isocyanate groups, with component (b) and, if desired, components (c) and (d).

In step I, carbodiimide structures are produced by conventional reaction of the isocyanate groups with one another, with elimination of carbon dioxide, in the presence of customary catalysts known for this reaction. In step II, isocyanate groups are reacted with isocyanate-reactive compounds in a conventional manner to produce urethane and/or urea structures.

The molar ratio of the NCO groups of the isocyanato-containing carbodiimide to the sum of the isocyanate-reactive groups of component (c) and the amino groups of component (a) is usually from 10:1 to 0.2:1, preferably from 5:1 to 0.5:1.

Alternatively, the carbodiimides of the invention may be obtained by reacting component (a) first with components (b) and, if desired, (c), the ratio of isocyanate groups used to the sum of the isocyanate-reactive groups of component (c) and the amino groups of component (b) being at least 2:1, and subsequently reacting the isocyanato-containing reaction product to carbodiimides, in the presence of catalysts and with release of carbon dioxide. In accordance with this process variant, up to 50% by weight, preferably up to 23% by weight, of the isocyanate groups of component (a) are first reacted with the isocyanate-reactive compounds and then some or all of the free isocyanate groups are reacted to carbodiimide groups in the presence of catalysts, with release of carbon dioxide.

The reactions may preferably be conducted in the presence of a solvent. Suitable solvents are in particular those compounds which readily dissolve the product of the reaction of step I and are also miscible with water, examples being methanol, ethanol, n- and/or isopropanol, propanone, tetrahydrofuran, dioxane, N-methylpyrrolidone, dimethylformamide, dimethylacetamide, and/or propylene carbonate. Preference is given to the use of solvents having a boiling point at 1013 mbar of less than 100° C.

The process step wherein the carbodiimide groups are formed may be conducted at elevated temperatures, e.g., at temperatures from 50 to 200° C., preferably from 150 to 185° C., judiciously in the presence of catalysts. Processes suitable for this purpose are described, for example, in GB-A-1 083 410, DE-B 1 130 594 (GB-A-851 936), and DE-A-11 56 401 (U.S. Pat. No. 3,502,722). Compounds which have proven excellent as catalysts are, for example, phosphorus compounds, selected preferably from the group consisting of phospholenes, phospholene oxides, phospholidines, and phospholine oxides. The polycarbodiimide formation is normally ended when the reaction mixture has the desired NCO group content. To accomplish this ending, the catalysts may be distilled off under reduced pressure or deactivated by adding a deactivator, such as phosphorus trichloride, for example. The preparation of the polycarbodiimides may also be conducted in the absence or presence of solvents which are inert under the reaction conditions.

The temperature during the step in which predominantly urethane and urea groups are formed is usually from 10 to 100° C.

If component (a) is reacted first to an isocyanato-containing carbodiimide (step I) and then the compound (V), the intermediate formed in step I preferably has an NCO content of from 1 to 18% by weight.

Through a suitable choice of the reaction conditions, such as, for example, the reaction temperature, the type and amount of catalyst, and the reaction time, the skilled worker is able to adjust the degree of condensation in the usual manner. The course of the reaction may most easily be monitored by determining the NCO content. Other parameters as well, such as, for example, viscosity increase, deepening of color, or $CO_2$ evolution, can be drawn upon for monitoring the progress of, and controlling, the reaction.

The compound (V) of the invention is suitable in particular for increasing the molecular weight of polymers (P) present in the form of an aqueous dispersion.

Suitable polymers (P) are virtually all film-forming polymers.

The polymers (P) preferably carry carboxyl groups, generally in amounts of from 0.01 to 2 mol/kg.

Mixtures of compounds (V) and aqueous dispersions comprising polymer (P) contain compounds (V) and polymer (P) preferably in a weight ratio of from 0.005:1 to 1:1.

The mixing operation is not critical and may be performed, for example, by stirring compound (V) into the aqueous dispersions comprising polymer (P). Mixing may be carried out at any desired point in time prior to their application.

Suitable polymers (P) are, for example, water-dispersible polyurethanes (polymers PII). Polyurethanes of this kind and the dispersions comprising them are common knowledge (cf. Ullmann's Encyclopedia of Industrial Chemistry, 5$^{th}$ Edition, Volume A 21, pages 677 f).

Preferably, dispersions of this kind are composed of
IIa) diisocyanates having 4 to 30 carbon atoms,
IIb) diols of which
　IIb1) from 10 to 100 mol %, based on the overall amount of the diols (IIb), have a molecular weight of from 500 to 5000, and
　IIb2) from 0 to 90 mol %, based on the overall amount of the diols, have a molecular weight of from 60 to 500 g/mol,
IIc) monomers other than the monomers (IIa) and (IIb), which have at least one isocyanate group or at least one isocyanate-reactive group and also carry at least one hydrophilic group or one potentially hydrophilic group, which makes the polyurethanes dispersible in water,
IId) if desired, further, polyfunctional compounds which are different from the monomers (IIa) to (IIc) and have reactive groups which are alcoholic hydroxyl groups, primary or secondary amino groups, or isocyanate groups, and
IIe) if desired, monofunctional compounds which are different from the monomers (IIa) to (IId) and have a reactive group which is an alcoholic hydroxyl group, a primary or secondary amino group, or an isocyanate group.

Suitable monomers (IIa) are the aliphatic or aromatic diisocyanates commonly used in polyurethane chemistry. Preference is given to the monomers (IIa) or mixtures thereof which are mentioned also as monomers (IIa) in DE-A-195 21 500.

Suitable monomers (IIb) and (IId) are preferably those specified in DE-A-195 21 500 as monomers (IIb) and (IId).

Monomers IIb1 are, for example, polyester diols or polyether diols.

The monomers IIb2 comprise, for example, aliphatic diols having 2 to 12 carbon atoms, e.g., 1,4-butanediol or 1,6-hexanediol.

Examples of suitable monomers (IId) are aliphatic amines having 2 to 12 carbon atoms and 2 to 4 groups selected from the group consisting of primary and secondary amino groups. Examples are ethylenediamine, isophoronediamine, and diethylenetriamine.

In order to render the polyurethanes dispersible in water they are synthesized not only from components (IIa), (IIb) and (IId) but also from monomers (IIc) which are different from components (IIa), (IIb) and (IId) and which carry at least one isocyanate group or at least one isocyanate-reactive group and, in addition, at least one hydrophilic group or a group which can be converted to a hydrophilic group. In the text below, the term hydrophilic groups or potentially hydrophilic groups is shortened to (potentially) hydrophilic groups. The (potentially) hydrophilic groups react with isocyanates much more slowly than do the functional groups of the monomers used to synthesize the polymer main chain.

Preferred monomers (IIc) are likewise those designated as monomers (IIc) in DE-A-195 21 500.

The proportion of components having (potentially) hydrophilic groups among the overall amount of components (IIa), (IIb), (IIc), (IId) and (IIe) is generally such that the molar amount of the (potentially) hydrophilic groups, based on the amount by weight of all monomers (a) to (e), is from 80 to 1200, preferably from 100 to 1000, and with particular preference from 150 to 800, mmol/kg.

The (potentially) hydrophilic groups can be nonionic groups, e.g., polyethylene oxide groups, or, preferably, (potentially) ionic hydrophilic groups, e.g., carboxylate groups or sulfonate groups. It is preferred to work without effective amounts of nonionic groups.

The amount of nonionic hydrophilic groups, if such are incorporated, is generally up to 5, preferably up to 3, with particular preference up to 1% by weight, based on the amount by weight of all monomers (IIa) to (IIe).

Monomers (IIe), which are used as well if desired, are monoisocyanates, monoalcohols, and mono-primary and mono-secondary amines. In general, their proportion is not more than 10 mol %, based on the overall molar amount of the monomers. These monofunctional compounds usually carry other functional groups, such as carbonyl groups, and serve to introduce functional groups into the polyurethane which allow the polyurethane to be dispersed and/or crosslinked or to undergo further polymer-analogous reaction.

Within the field of polyurethane chemistry it is generally known how the molecular weight of the polyurethanes can be adjusted by choosing the proportions of the co-reactive monomers and by the arithmetic mean of the number of reactive functional groups per molecule.

Components (IIa) to (IIe) and their respective molar amounts are normally chosen so that the ratio A:B, where
A) is the molar amount of isocyanate groups, and
B) is the sum of the molar amount of the hydroxyl groups and the molar amount of the functional groups which are able to react with isocyanates in an addition reaction, is from 0.5:1 to 2:1, preferably from 0.8:1 to 1.5, with particular preference from 0.9:1 to 1.2:1. With very particular preference, the ratio A:B is as close as possible to 1:1.

Furthermore, the proportion of the monomers (a) is preferably chosen so that the proportion of the monomers (IIa) among the monomers (IIa) to (IIe) is from 20 to 70% by weight.

The monomers (IIa) to (IIe) that are employed carry on average usually from 1.5 to 2.5, preferably from 1.9 to 2.1, with particular preference 2.0, isocyanate groups and/or functional groups which are able to react with isocyanates in an addition reaction.

The various preparation methods of the polymers PII are common knowledge and are described in more detail, for example, in DE-A-198 07 754.

The polymers (P) may further comprise conventional emulsion polymers (polymers PIII).

These are composed in general of

IIIa) from 30 to 99.9% by weight of principal monomers selected from $C_1$ to $C_{20}$ alkyl (meth)acrylates, vinyl esters of carboxylic acids containing up to 20 carbon atoms, vinylaromatic compounds having up to 20 carbon atoms, ethylenically unsaturated nitriles, vinyl halides, and aliphatic hydrocarbons having 2 to 8 carbon atoms and 1 or 2 double bonds, IIIb) from 0 to 20, preferably from 0.01 to 20, % by weight of a carboxylic acid having an olefinic double bond, and IIIc) from 0 to 20% by weight of free-radically polymerizable monomers other than (IIIa) and (IIIb).

Examples that may be mentioned of monomers (IIIa) are (meth)acrylic acid alkyl esters having a $C_1$–$C_{10}$ alkyl radical, such as methyl methacrylate, methyl acrylate, n-butyl acrylate, ethyl acrylate, and 2-ethylhexyl acrylate.

Also suitable, in particular, are mixtures of the (meth) acrylic acid alkyl esters.

Vinyl esters of carboxylic acids having 1 to 20 carbon atoms are, for example, vinyl laurate, vinyl stearate, vinyl propionate, and vinyl acetate.

Suitable vinylaromatic compounds are vinyltoluene, alpha- and p-methylstyrene, alpha-butylstyrene, 4-n-butylstyrene, 4-n-decylstyrene and, preferably, styrene.

Examples of nitriles are acrylonitrile and methacrylonitrile.

The vinyl halides are chloro-, fluoro- or bromo-substituted ethylenically unsaturated compounds, preferably vinyl chloride and vinylidene chloride.

Nonaromatic hydrocarbons having 2 to 8 carbon atoms and one or two olefinic double bonds include butadiene, isoprene, and chloroprene, and also ethylene, propylene, and isobutylene.

The principal monomers (IIIa) are also, preferably, used in a mixture.

Vinylaromatic compounds such as styrene are, for example, frequently used in a mixture with $C_1$–$C_{20}$ alkyl (meth)acrylates, in particular with $C_1$–$C_8$ alkyl (meth)acrylates, or with nonaromatic hydrocarbons such as isoprene or, preferably, butadiene.

Suitable monomers (IIIb) are preferably (meth)acrylic acid or maleic acid.

Examples of suitable monomers (IIIc) include the following: esters of acrylic and methacrylic acid with alcohols having 1 to 20 carbon atoms, containing as well as the oxygen atom in the alcohol group at least one further heteroatom and/or an aliphatic or aromatic ring, such as 2-ethoxyethyl acrylate, 2-butoxyethyl(meth)acrylate, dimethylaminoethyl (meth)acrylate, diethylaminoethyl (meth) acrylate, (meth)acrylic aryl, alkaryl or cycloalkyl esters, such as cyclohexyl (meth)acrylate, phenylethyl (meth)acrylate, phenylpropyl (meth)acrylate, or acrylic esters of heterocyclic alcohols, such as furfuryl (meth)acrylate.

Also suitable as monomer (IIIc) are monomers having amino groups or amide groups, such as (meth)acrylamide, and derivatives thereof substituted on the nitrogen by $C_1$–$C_4$ alkyl.

Of particular importance as monomers (IIIc) are hydroxyfunctional monomers, e.g., (meth)acrylic acid $C_1$–$C_{15}$ alkyl esters substituted by one or two hydroxyl groups. Of particular importance as hydroxy-functional comonomers are (meth)acrylic acid $C_2$–$C_8$ hydroxyalkyl esters, such as n-hydroxyethyl, n-hydroxypropyl or n-hydroxybutyl (meth)acrylate.

The polymer (PIII) is prepared by free-radical polymerization. Appropriate methods of polymerization, such as bulk, solution, suspension, or emulsion polymerization, are known to the skilled worker.

The copolymer is preferably prepared by solution polymerization with subsequent dispersion in water or, with particular preference, by emulsion polymerization.

In the case of emulsion polymerization the comonomers can be polymerized as usual in the presence of a water-soluble initiator and an emulsifier at preferably from 30 to 95° C.

Examples of suitable initiators are sodium, potassium and ammonium persulfate, tert-butyl hydroperoxides, water-soluble azo compounds, or redox initiators.

Examples of emulsifiers used are alkali metal salts of relatively long-chain fatty acids, alkyl sulfates, alkyl sulfonates, alkylated arylsulfonates or alkylated biphenyl ether sulfonates. Further suitable emulsifiers are reaction products of alkylene oxides, especially ethylene oxide or propylene oxide, with fatty alcohols or fatty acids or with phenols, or alkylphenols.

In the case of aqueous secondary dispersions, the copolymer is first prepared by solution polymerization in an organic solvent and is then dispersed in water with the addition of salt formers, e.g., ammonia, to carboxyl-containing copolymers, without the use of an emulsifier or dispersing auxiliary. The organic solvent may be removed by distillation. The preparation of aqueous secondary dispersions is known to the skilled worker and is described, for example, in DE-A-37 20 860.

To adjust the molecular weight it is possible to use regulators during the polymerization. Suitable examples are —SH-containing compounds such as mercaptoethanol, mercaptopropanol, thiophenol, thioglycerol, ethyl thioglycolate, methyl thioglycolate, and tert-dodecyl mercaptan; they can be used additionally, for example, in amounts of from 0 to 0.5% by weight, based on the copolymer.

The nature and amount of the comonomers are preferably chosen such that the resulting copolymer has a glass transition temperature of from −60 to +140° C., preferably from −60 to +100° C. The glass transition temperature of the copolymer is determined by means of differential thermal analysis or differential scanning calorimetry in accordance with ASTM 3418/82.

The number-average molecular weight, $M_n$, is preferably from $10^3$ to $5\times10^6$, with particular preference from $10^5$ to $2\times10^6$ g/mol (as determined by gel permeation chromatography using polystyrene as standard).

The polymers (P) may further comprise (polymers PIV) a water-dispersible polyester which carries carboxyl groups.

The water-dispersible polyesters which carry carboxyl groups (polymer IV) are known, for example, from Encyclopedia of Polymer Science and Engineering, John Wiley & Sons, Second Edition, Volume 12, pages 300 to 313.

The aqueous dispersions comprising the polymer (P) usually have a solids content of from 10 to 70% by weight.

The mixtures of the invention comprising compound (V) and polymer (P) may comprise commercially customary auxiliaries and additives such as wetting agents, defoamers, flatting agents, emulsifiers, thickeners and thixotropic agents, and colorants such as dyes and pigments.

They are suitable, for example, for the adhesive bonding or coating of various substrates such as wood, metal, plastic, paper, leather or textile, for the impregnation of textiles, and for the production of moldings and printing inks.

In these contexts, the dispersions of the invention may be processed by the techniques commonplace in the adhesives, leather or coatings industry, i.e., by spraying, rolling or knife-coating the dispersions onto the substrate and then drying them.

For the case of processing as an adhesive, the coated workpieces are joined to another workpiece, preferably with application of pressure, either before or after the dispersion film has dried.

Particularly strong adhesive bonds are obtained if workpieces that have been provided with a dried adhesive film are heated to a temperature of from about 50 to 100° C. directly before, during, or after joining.

The adhesive bonds produced by these methods are particularly notable for their storage stability and their high thermal stability.

Furthermore, the compounds V may be used to produce adhesive sheets. This is done by blending aqueous dispersions comprising a polymer (PII) or (PIII) with the compound (V). This blend is applied by the customary, above-mentioned methods to polymer films, preference being given to corona-treated polyethylene film. The amounts applied are usually from 5 to 6 g/m².

Coated adhesive sheet comprising corona-treated polyethylene film is suitable for sticking to articles of all kinds. If use is made of a sheet of this kind with a mixture of a compound (V) and a polymer (PII) or (PIII) that may be used as a pressure-sensitive adhesive, then the coated sheet is notable in particular for the fact that it can be detached from the substrate without residue along with polymer (PII) or (PIII). The fact that the layer of adhesive formed from polymer (PII) or (PIII) adheres better to the polyethylene film than to the substrate and exhibits high cohesion is something we attribute to the fact that the compound (V) increases the molecular weight of the polymer (PII) or (PIII) and at the same time anchors it to the polyethylene film with the formation of covalent bonds, the carbodiimide groups of the compound (V) probably reacting with those carboxyl groups on the surface of the polyethylene film which come about during the corona treatment.

Adhesive sheets of this kind are therefore particularly suitable for producing labels or for use as protective sheets in order to protect articles, especially those having sensitive surfaces such as coated surfaces or those made of plexiglass, polycarbonate or glass, e.g., screens or windows, against mechanical damage, e.g., scratches, or other environmental influences in the course of storage and transit. They possess the additional advantage that they have a good tack, i.e., the film adheres to the substrate just on contact, without the use of high pressure, e.g., by brushing with the hand or by placing the sheet on the substrate, and can be peeled from the substrate again with moderate force (e.g., using from 1.25 to 2.5 N in the case of an adhesive strip having a width of 25 mm).

Experimental Section

1. Preparing the Carboxyl-carbodiimides
   1.1. With Dimethylolpropionic Acid
   A solution of 500 g of a NCO-terminated carbodiimide from TMXDI, having an NCO content of 7.8% by weight, in 100 g of acetone was added to a solution of 67 g (0.5 mol) of DMPA and 60.0 g (0.593 mol) of triethylamine (TEA) in 100 g of acetone, with stirring. After 240 minutes of stirring at 60° C., the mixture was diluted with 2000 g of water and the acetone was stripped off under reduced pressure.
   This gives a colloidal, aqueous solution of a carbodiimide, having a solids content of 22% and an LT of 100.
   1.2. With Hydroxypivalic Acid
   A solution of 250 g of a NCO-terminated carbodiimide from TMXDI, having an NCO content of 7.8% by weight, in 50 g of acetone was added to a solution of 59 g (0.5 mol) of hydroxypivalic acid and 60.0 g (0.593 mol) of triethylamine (TEA) in 100 g of acetone, with stirring. After 240 minutes of stirring at 60° C., the mixture was diluted with 1200 g of water and the acetone was stripped off under reduced pressure.
   This gives a colloidal, aqueous solution of a carbodiimide, having a solids content of 23% and an LT of 100.

2. Use Examples
   Use Example 2.1: Use in Leather Dressing
   For testing as a leather dressing, a spray liquor having the following composition was prepared:

45.7 p Astacin® Top GA 45.5 p deionized water 0.5 p Lepton® paste VL 1.0 p Lepton® wax LD6609.

Astacin Top GA is a polyester-polyurethane dispersion having a solids content of 30% by weight.

Lepton paste VL is a urethane-based associative thickener.

Lepton wax LD 6609 is a silicone-based hand agent.

This liquor was admixed in Use Example A1.1. with 7.8 p, in Use Example A1.2. with 15.5 p, of the solution from Example 1.1.

In the comparative example, C1, no solution was added.

The liquors were sprayed at a rate of 10 g/DIN A4 onto bottomed calf box leather and dried at A) 10 min/80° C. and B) 12 h/80° C.

The leathers were conditioned for 2 days at 23° C. and 50% relative atmospheric humidity and then subjected to a physical leather test, with the following results:

| Finish batches: | C1 | A1.1 | A1.2 |
|---|---|---|---|
| Veslic wet rub test | 100× g-d | 300× g | 400× g |
| A) | 250× s | 400× d-s | 500× d-s |
| B) | 300× d-s | 900× d-s | 1300× d |
| Flexometer test 50,000 × dry A) | gray/d* | 0* | 0 |
| Flexometer test 20,000 × wet A) | gray/g-d* | 0 | 0 |
| Flexometer test 50,000 × dry B) | g* | 0 | 0 |
| Flexometer test 20,000 × wet B) | gray/g* | 0 | 0 |

Evaluation:
0 = no damage;
g = slight damage;
d = distinct damage;
s = severe damage;
* = sticking occurs at site of pressing Use Example 2.2: Use to Produce Protective Sheets Preparing a polymer dispersion:

| | Initial charge (g) | Monomer emulsion (g) | Initiator (g) | After catalysis |
|---|---|---|---|---|
| Water | 260 | 200 | | 35.10 |
| Emulsifier solution 1 | | 24 | | |
| Emulsifier solution 2 | | 8 | | |
| 2-EHA | | 214.5 | | |
| nBA | | 450.45 | | |
| MMA | | 21.45 | | |
| M-Amol | | 95.33 | | |
| AA | | 14.3 | | |
| NaPS 5% solution in water | | | 71.5 | |
| NH$_3$ 25% solution in water | | | | 13.5 |
| t-BHP 10% solution in water | | | | 21.45 |
| Acetone | | | | 1.36 |
| Na disulfite | | | | 2.15 |

Emulsifier solution 1: 30% strength by weight solution of the sodium salt of a sulfuric monoester mixture of C10–C16 alkyl ethoxylates (average EO degree 30) in water (Disponil® FES 77 from Henkel KGaA)
Emulsifier solution 2: 45% strength by weight solution of (dodecyl-sulfonyl-phenoxy)benzenesulfonic acid sodium salt (Dowfax® 2A1 from Dow Chemicals)

Procedure:

The initial charge was placed in a 2 liter flask with reflux condenser, nitrogen inlet, and metal stirrer. It was brought to 90° C. under nitrogen blanketing. 20% of the initiator solution were added. After 5 minutes, the monomer emulsion was added over the course of 3 hours. At the same time, the remaining initiator solution was added over the course of 3.5 hours. After the end of the initiator feed, polymerization was continued for 30 minutes. The mixture was then cooled to 80° C. and the after-catalyst solution and ammonia were added.

The two t-BHP and acetone/Na disulfite feeds were added in parallel over the course of 1 hour. Subsequently, the dispersion was cooled to room temperature.

The solids content of the dispersion is 51%; the pH is 7. The particle size is 280 nm (as determined by means of a Malvern autosizer).

Application: Protective Sheet

Producing the Protective Sheets

The dispersion was mixed with 1.5% (solids/solids) (A2.1.) or with 3% (solids/solids) (A2.2.) of the solution from Example 1.1. For comparison, a mixture was prepared from the dispersion with 1.5% Basonat® FDS 3425 (C2).

The mixtures were knife coated at from 5 to 6 g/m$^2$ onto a corona-treated polyethylene film and dried at 90° C. for three minutes. The films were lined with silicone paper and stored at room temperature for three days.

Testing for Removal Without Residue:

This test consists in evaluating the appearance of the protected surface following the removal of the protective sheet. The surface to which the sheet is stuck is stored for one and four weeks at 50° C. and 80% relative atmospheric humidity. The sheets are then peeled off by hand, slowly in one instance and rapidly in another, and the residue on the surface is assessed visually. In the best case, the surface is free from residues of the adhesive.

Evaluation is Made in Accordance With the Following Scale:
1 no residue
1* negative impression of the protective sheet (shadows at the edge, no shadows otherwise)
2 shadow of the protective sheet
3 residue perceptible
4 partial transfer of the adhesive
5 complete transfer of the adhesive
6 cohesive fracture The peel behavior is assessed in accordance with the following scale:
A slightly tacky
B easy to remove
C difficult to remove Tests were carried out on steel, polycarbonate, and plexiglass.

The optimum rating is B1.

Results of the removal test.

| Dispersion | Removal | Plexiglass 1 week | Plexiglass 4 weeks | Polycarbonate 1 week | Polycarbonate 4 weeks | Steel 1 week | Steel 4 weeks |
|---|---|---|---|---|---|---|---|
| Dispersion without crosslinker | slow | B1 | B1 | B1 | B1 | B1* | B2 |
|  | rapid | B1 | B1 | B1 | B1 | B3 | B3 |
| Dispersion +1.5% Basonat FDS3425 | slow | B1 | B1 | B1 | B1 | B2 | B2 |
|  | rapid | B1 | B1 | B1 | B1 | B2 | B3 |
| Dispersion +1.5% solution 1.1 | slow | B1 | B1 | B1 | B1 | B2 | B1* |
|  | rapid | B1 | B1 | B1 | B1 | B2 | B2 |
| Dispersion +3% solution 1.1 | slow | B1 | B1 | B1 | B1 | B1* | B1* |
|  | rapid | B1 | B1 | B1 | B1 | B1* | B2 |

Quick Stick, Peel Strength, and Scratch Test on PE Film:

The dispersions were knife-coated at 20 g/m² onto 25 mm wide sections of PE film and dried at 90° C. for 3 minutes.

The protective sheets obtained in this way were bonded to a steel plate and the "quick stick" and peel strength were tested at 23° C. and 50% relative atmospheric humidity.

The quick stick test is one of the best-known methods of measuring tack (tack is the ability of a pressure-sensitive adhesive to adhere immediately to a surface). In the quick stick method (FINAT method) a test strip is looped, brought into contact with a glass plate, and peeled off again immediately thereafter.

The adhesion of the dispersion to the sheet is tested by means of the scratch test: the more difficult it is to scratch off the film with the finger, the better the adhesion of the dispersion.

Peel rate: 300 mm/min

| | Quick stick N/25 mm steel | | Peel strength in N/25 mm steel immediate | | 24 hours | | scratch test |
|---|---|---|---|---|---|---|---|
| Dispersion without crosslinker | 3.5 | A | 1.8 | A | 6.2 | A | 3 |
| Dispersion + 1.5% Bas. FDS 3425 | 2.4 | A | 1.1 | A | 4.6 | A | 1 |
| Dispersion + 1.5% carbodiimide 1.1 | 3.1 | A | 1.5 | A | 6.5 | A | 1–2 |
| Dispersion + 3.0% carbodiimide 1.1 | 2.6 | A | 1.2 | A | 6.3 | A | 1 |

Scratch test
1 = no scratch removal
2 = difficult to remove by scratching
3 = easy to remove by scratching 3. Determining the Crosslinking Density by Measuring the Dynamic Shear Modulus of Films:

On films with and without carbodiimide or Basonat, the storage modulus G' and the loss modulus G" were measured as a function of temperature. The films were thermally conditioned at 90° C. for 10 minutes.

Storage moduli at 100° C.

| Sample | G' at 100° C. (×10⁴ Pa) |
|---|---|
| Dispersion without crosslinker | 4.98 |
| Dispersion + 1.5% Bas. FDS 3425 | 6.46 |
| Dispersion + 1.5% carbodiimide 1.1 | 5.81 |
| Dispersion + 3.0% carbodiimide 1.1 | 7.17 |

The additions increase the storage modulus at high temperatures, which is a measure of the crosslinking density.

Abbreviations
nBA: n-butyl acrylate
MMA: methyl methacrylate
M-Amol: methylolmethacrylamide
AA: acrylic acid
NaPS: sodium peroxodisulfate
t-BHP: tert-butyl hydroperoxide
NH$_3$: ammonia
2-EHA: 2-ethyl hexylacrylate
P.: parts

We claim:

1. A compound with carbodiimide units and carboxyl or carboxylate groups (compound V), derived from components consisting of:
    a) aliphatic or araliphatic $C_4$ to $C_{20}$ polyisocyanates (component a)
    b) hydroxy carboxylic acids or hydroxy carboxylic salts (component b) wherein component a and component b are first reacted together to form a reaction product and
    c) optionally, further reacting the reaction product of component a and component b with compounds, having 1 to 20 carbon atoms and containing hydroxyl and/or amino groups as isocyanate reactive groups in an addition reaction and having a molecular weight of less than 400 g/mol (component c) and
    d) optionally, other isocyanates (component d), the carbodiimide units being derived essentially exclusively from the isocyanate groups of component a).

2. A compound (V) as claimed in claim 1, containing from 200 to 2000 mmol/kg of carboxyl or carboxylate groups, based on the weight of the compound.

3. A compound (V) as claimed in claim 1, wherein component (a) is hexamethylene diisocyanate or 1,3-bis(1-methyl-1-isocyanatoethyl)benzene.

4. A compound (V) as claimed in claim 1, wherein the hydroxy carboxylic acids or hydroxy carboxylic salts are carboxylic acids or salts, respectively, having one or two hydroxyl groups.

5. A compound (V) as claimed in claim 1, wherein the compound (V) includes component (c), and component (c) is an aromatic, aliphatic or, araliphatic compound carrying polyalkylene oxide groups, having 1 to 20 carbon atoms, wherein the number of carbon atoms does not include those of the polyalkylene oxide groups, and at least one functional group selected from the group consisting of secondary amino groups, primary amino groups, and alcoholic hydroxyl groups.

6. A process for preparing a compound (V) as claimed in claim 1, which comprises
   III. preparing carbodiimides having terminal isocyanate groups, by carbodiimidizing some of the isocyanate groups of component (a), and
   IV. reacting the compounds prepared in step III, having terminal isocyanate groups, with component (b) and, optionally, components (c) and (d).

7. A mixture of a compound (V) as claimed in claim 1 and an aqueous dispersion comprising a polymer (P).

8. A mixture as claimed in claim 7, wherein the polymer (P) carries carboxyl groups.

9. A mixture as claimed in claim 7, wherein polymer (P) comprises a polyurethane (PII) composed of
   IIa) Diisocyanates having 4 to 30 carbon atoms,
   IIb) Diols of which from 0 to 90 mol%, based on the overall amount of the diols (IIb), have a molecular weight of from 60 to 400 g/mol,
   IIc) monomers other than the monomers (IIa) and (IIb), which have at least one isocyanate group or at least one isocyanate-reactive group and also carry at least one hydrophilic group or one potentially hydrophilic group, which makes the polyurethanes dispersible in water,
   IId) optionally, further, polyfunctional compounds which are different from the monomers (IIa) to (IIc) and have reactive groups which are alcoholic hydroxyl groups, primary or secondary amino groups, or isocyanate groups, and
   IIe) optionally, monofunctional compounds which are different from the monomers (IIa) to (IId) and have a reactive group which is an alcoholic hydroxyl group, a primary or secondary amino group, or an isocyanate group.

10. A mixture as claimed in claim 7, wherein polymer (P) comprises a polymer (PIII) composed of
   IIIa) from 30 to 99.9% by weight of principal monomers selected from $C_1$ to $C_{20}$ alkyl (meth)acrylates, vinyl esters of carboxylic acids containing up to 20 carbon atoms, vinylaromatic compounds having up to 20 carbon atoms, ethylenically unsaturated nitriles, vinyl halides, and aliphatic hydrocarbons having 2 to 8 carbon atoms and 1 or 2 double bonds,
   IIb) from 0 to 20% by weight of a carboxylic acid having an olefinic double bond, and
   IIIc) from 0 to 20% by weight of free-radically polymerizable monomers other than (IIIa) and (IIIb).

11. An article bonded or coated with the mixture as claimed in claim 7, or a textile impregnated with said mixture.

* * * * *

UNITED STATES PATENT AND TRADEMARK OFFICE
CERTIFICATE OF CORRECTION

| | | |
|---|---|---|
| PATENT NO. | : 7,049,001 B2 | Page 1 of 1 |
| APPLICATION NO. | : 10/169070 | |
| DATED | : May 23, 2006 | |
| INVENTOR(S) | : Häberle et al. | |

It is certified that error appears in the above-identified patent and that said Letters Patent is hereby corrected as shown below:

On the title page, the Terminal Disclaimer information has been omitted. Item (45) and the Notice Information should read:

-- [45] Date of Patent:  * May 23, 2006

[*] Notice: Subject to any disclaimer, the term of this patent is extended or adjusted under 35 U.S.C. 154(b) by 268 days.

This patent is subject to a terminal disclaimer.--

Signed and Sealed this

Twenty-fourth Day of October, 2006

JON W. DUDAS
*Director of the United States Patent and Trademark Office*